US008148705B2

(12) United States Patent
Hirose et al.

(10) Patent No.: US 8,148,705 B2
(45) Date of Patent: Apr. 3, 2012

(54) METHOD AND APPARATUS FOR INSPECTING DEFECTS OF PATTERNS FORMED ON A HARD DISK MEDIUM

(75) Inventors: Takenori Hirose, Yokohama (JP); Masahiro Watanabe, Yokohama (JP); Yasuhiro Yoshitake, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 527 days.

(21) Appl. No.: 12/314,938

(22) Filed: Dec. 19, 2008

(65) Prior Publication Data
US 2009/0161244 A1 Jun. 25, 2009

(30) Foreign Application Priority Data

Dec. 21, 2007 (JP) ................................. 2007-330482

(51) Int. Cl.
*G01N 21/86* (2006.01)
*G01V 8/00* (2006.01)

(52) U.S. Cl. ........... 250/559.44; 250/559.4; 250/559.45; 356/237.2; 356/237.3; 356/394

(58) Field of Classification Search .. 250/559.4–559.45; 356/237.2, 237.3, 237.4, 237.5, 394
See application file for complete search history.

(56) References Cited

U.S. PATENT DOCUMENTS

| 2002/0180961 | A1* | 12/2002 | Wack et al. | 356/237.2 |
| 2005/0024633 | A1* | 2/2005 | Nishiyama et al. | 356/237.2 |
| 2006/0222235 | A1* | 10/2006 | Kanegae | 382/145 |

FOREIGN PATENT DOCUMENTS

| JP | 2000-180376 | 6/2000 |
| JP | 2000-310512 | 11/2000 |
| JP | 2005-127830 | 5/2005 |

* cited by examiner

*Primary Examiner* — Francis M Legasse, Jr.
(74) *Attorney, Agent, or Firm* — Antonelli, Terry, Stout & Kraus, LLP.

(57) ABSTRACT

If an inspection method for inspecting a patterned medium is intended for the nanoimprint process control, it is necessary to measure a correct shape of each pattern element. On the other hand, if the inspection method is intended for the quality control of products, it is necessary to inspect the products on a 100 percent basis. However, the conventional method which uses SEM or AFM could not satisfy these requirements. According to the present invention, 100-percent inspection of products becomes possible by a method including the steps of: irradiating a surface of a hard disk medium, on which a magnetic material pattern is formed, with a light beam including a plurality of wavelengths; detecting the intensity of a reflected light beam from the hard disk medium on a wavelength basis; calculating a spectral reflectance from the detected intensity of the reflected light beam; and detecting a shape of each pattern element formed on the hard disk medium on the basis of the calculated spectral reflectance.

18 Claims, 11 Drawing Sheets

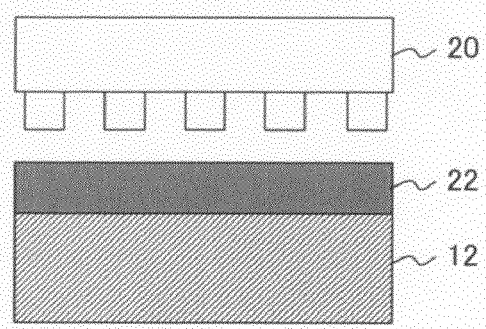
FIG. 3A
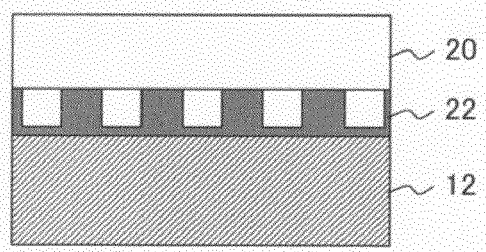
FIG. 3B
FIG. 3C
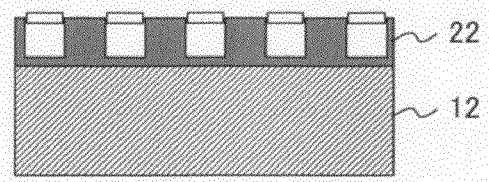
FIG. 3D
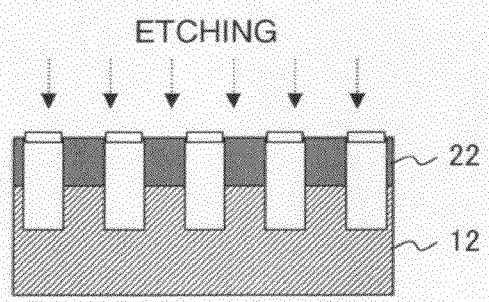
FIG. 3E
FIG. 3F
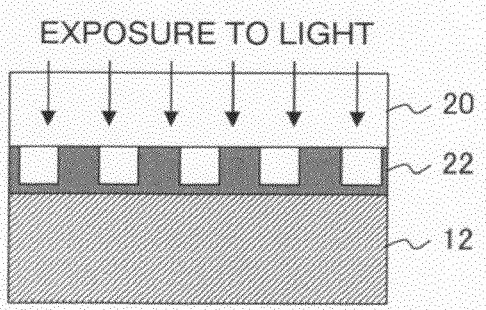
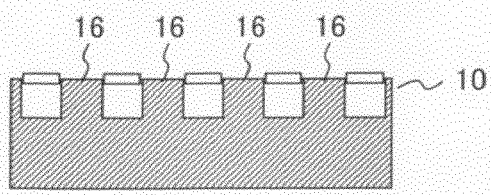

EMA

METHOD AND APPARATUS FOR INSPECTING DEFECTS OF PATTERNS FORMED ON A HARD DISK MEDIUM

BACKGROUND OF THE INVENTION

The present invention relates to inspection performed in a manufacturing process of hard disk media and more particularly to a technique for detecting the shapes of patterns formed on a patterned medium and thereby to detect defectively shaped patterns.

In recent years, the application of hard disk drives to severs and computers has been increasing; at the same time, the application of them has been extending to other purposes such as home-use hard disk recorders, car navigation systems, and portable audio-visual reproducing devices. The capacity of hard disk drives has also been increasing with the digitalization of various devices.

Increasing the capacity of a hard disk drive means increasing the recording density of a medium disk. As one of the technologies for increasing the recording density of a medium disk, a patterned medium is expected to be introduced in the future. As shown in FIG. 2, there are two kinds of patterned media: a discrete track medium, and a bit patterned medium. The discrete track medium is based on a method in which a concentric circular track pattern 14 is formed on the medium disk 10 as shown on the left side of FIG. 2. The bit patterned medium is based on a method in which an infinite number of bit patterns 16 are formed as shown on the right side of FIG. 2.

Heretofore, a magnetic film is formed on a surface of a disk; and the magnetic film is then divided into in areas, each of which corresponds to one bit. Data is recorded by magnetizing each of the areas. In contrast, when a patterned medium is used, a magnetic material is used to form pattern elements on a surface of a disk as described above. Magnetic information is recorded to the formed pattern elements. Adjacent pattern elements are spaced apart from each other so that they are magnetically insulated from each other. This makes it possible to increase the recording density in comparison with the conventional continuous film medium that is provided with no space.

Nanoimprint technique is used for the formation of a pattern, which is a prevailing method. As shown in FIG. 3A, the nanoimprint technique uses a mold 20 through which a light beam passes, and a photoresist 22 that is applied to a surface of a disk substrate 12 on which a magnetic film is formed. A light beam passes through the mold 20. According to the nanoimprint technique, the mold 20 is pressed against the photoresist 22 applied to the surface of the disk substrate 12 (FIG. 3B); while this state is kept, the photoresist 22 is exposed to a light beam (FIG. 3C); after the mold 20 is removed (FIG. 3D), etching is performed (FIG. 3E); and consequently, a bit pattern is formed (FIG. 3F). In this case, if the mold 20 in itself is defective, or if a foreign particle adheres to the mold 20, a defect will also occur in a transferred pattern. Therefore, the introduction of the nanoimprint technique requires the execution of new inspection as to whether or not a bit pattern is properly formed.

Heretofore, as an inspection method for detecting a defect on a surface of a continuous film disk, there is a method described in JP-A-2000-180376. This method includes the steps of: irradiating a surface of a disk with a laser light beam; properly selecting a signal obtained from a light receiving element for detecting both a regular reflected light beam from the surface of the disk and scattered light; and performing processing corresponding to the signal so as to correctly identify a kind of defect. In particular, discrimination between a linear defect and a planar defect, or discrimination between a concave defect and a convex defect, can be correctly performed.

The defect inspection described in JP-A-2000-180376 is intended to discriminate between a linear defect and a planar defect, or between a concave defect and a convex defect, on a surface of a continuous film disk. The defect inspection in question does not make a judgment as to whether or not a bit pattern is properly formed on a patterned medium.

As a method for inspecting a minute pattern element whose size is several tens of nanometers, the use of SEM and AFM can be considered. However, when a SEM (scanning electron microscope) is used, only a shape of a pattern element formed on a surface, which is viewed from the top, can be inspected. If a cross-sectional shape of the pattern element is inspected, the pattern element must be broken. On the other hand, when an AFM (atom force microscope) is used, a three dimensional shape of a target pattern element can be measured. However, the measurement result varies depending on a state of a probe. Accordingly, there is a case where a shape of a pattern element cannot be correctly measured. In addition, from the viewpoint of throughput, 100-percent product inspection cannot be carried out by these methods. Moreover, only a limited area on a disk can be inspected.

If the inspection is intended for the nanoimprint process control, it is necessary to measure a correct shape of each pattern element. In contrast, if the inspection is intended for the quality control of products, it is necessary to inspect the whole surface of the disk on a 100-percent product basis. The above methods cannot satisfy these requirements.

SUMMARY OF THE INVENTION

The present invention has been made to solve the above-described problems. According to one aspect of the present invention, there is provided an inspection method for inspecting a hard disk medium, said inspection method including the steps of: irradiating a surface of the hard disk medium, on which a pattern is formed, with a light beam including a plurality of wavelengths; detecting the intensity of a reflected light beam from the hard disk medium on a wavelength basis; calculating a spectral reflectance from the detected intensity of the reflected light beam; and detecting a shape of a pattern element formed on the hard disk medium on the basis of the calculated spectral reflectance.

According to another aspect of the present invention, there is provided an inspection apparatus for inspecting a hard disk medium, said inspection apparatus including: irradiation means for irradiating a surface of the hard disk medium, on which a pattern is formed, with a light beam including a plurality of wavelengths; spectral detection optical means for detecting the intensity of a reflected light beam from the surface of the hard disk medium on a wavelength basis; means for holding the hard disk medium, and for moving the hard disk medium or the spectral detection optical means so that the spectral detection optical means can detect the intensity of the reflected light beam at an arbitrary position on the surface of the hard disk medium; and a data processing unit for calculating a spectral reflectance from the intensity of the reflected light beam, which has been detected by the spectral detection optical means, and for detecting a shape of the pattern element formed on the hard disk medium, or judging whether or not the shape is defective, on the basis of the calculated spectral reflectance.

According to the present invention, a shape of a pattern element formed on a patterned medium can be correctly estimated. In addition, pattern shape inspection can be performed with high throughput on the whole surface of a patterned medium by using both the optical technique and the high-speed rotatable stage in combination. These and other objects, features and advantages of the invention will be apparent from the following more particular description of preferred embodiments of the invention, as illustrated in the accompanying drawings.

BRIEF DESCRIPTION OF THE DRAWINGS

FIG. 3A is a diagram illustrating a mold 20 through which a light beam passes, and a disk substrate 12 on which a photoresist 22 is applied to a surface of a magnetic film, the mold 20 and the disk substrate 12 being used in a nanoimprint process;

FIG. 3B is a diagram illustrating a state in which the mold 20 through which a light beam passes is pressed against the photoresist 22 that is applied to the surface of the disk substrate 12;

FIG. 3C is a diagram illustrating a state in which the photoresist 22 is exposed to a light beam with the mold 20 pressed against the photoresist 22;

FIG. 3D is a diagram illustrating a state in which the mold 20 is removed after the exposure to the light beam;

FIG. 3E is a diagram illustrating a state in which the photoresist 22 on which a mold pattern has been formed is subjected to etching;

FIG. 3F is a diagram illustrating a state in which a bit pattern has been formed on the surface of the disk substrate 12 as a result of the etching;

DESCRIPTION OF THE PREFERRED EMBODIMENTS

Figure 4A:
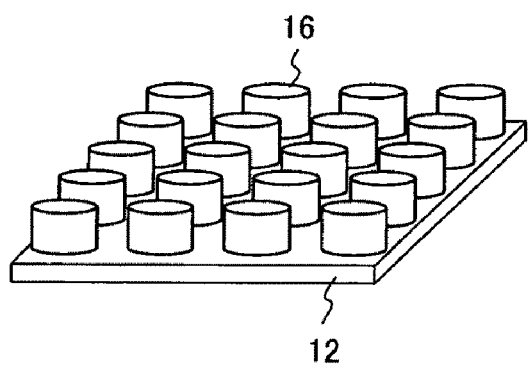
FIG. 4A is a diagram illustrating an example of a pattern in which the width of each pattern element is relatively wide.
Figure 4B:
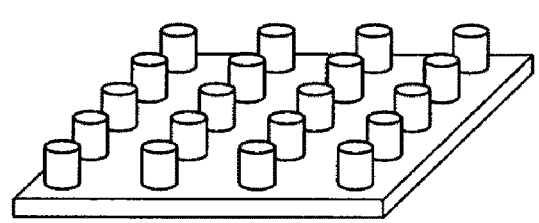
FIG. 4B is a diagram illustrating an example of a pattern in which the width of each pattern element is relatively narrow.
Figure 5:
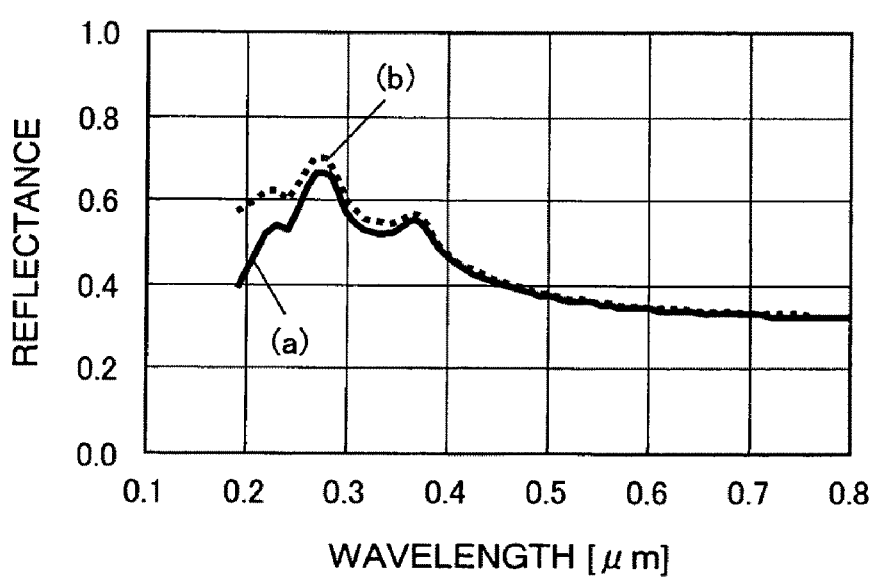
FIG. 5 is a graph illustrating spectral reflectance of surfaces of two kinds of patterns shown in FIGS. 4A, 4B respectively, the width of each pattern element included in the pattern shown in FIG. 4A differing from that of each pattern element included in the pattern shown in FIG. 4B.

First, a method for optically detecting the shape of each pattern element formed on a disk will be described. In the case of a patterned medium for which the present invention is mainly intended, pattern elements, each having a size of about several tens of nanometers, are periodically formed on a disk. In this case, if the height or width of each pattern element changes, so does the spectral reflectance of the whole surface on which the pattern elements are formed. For example, FIG. 5 is a graph showing the spectral reflectances of the two surfaces on which are formed the two patterns of FIGS. 4A and 4B, respectively, with different pattern element widths. FIG. 5 reveals that a different pattern shape results in a different spectral reflectance. Therefore, by detecting the spectral reflectance of a target surface, the shapes of pattern elements can be detected.

One of such methods for detecting the shapes of periodic, minute pattern elements is scatterometry. For example, by use of an electromagnetic-wave analysis technique such as RCWA (rigorous coupled-wave analysis), the spectral reflectance of a target surface can be obtained from the optical constant of the material or shape of a pattern element. In this method, the spectral reflectances of various pattern surfaces are calculated beforehand, using various parameters which indicate pattern shapes such pattern heights and widths. Then, the reflectance of a particular pattern surface is detected and compared with each of the reflectances calculated beforehand to find the reflectance closest to the detected reflectance, whereby the shapes of the pattern elements can be detected. Alternatively, the reflectance calculated with the use of the above-mentioned RCWA is fitted into the detected reflectance with values indicating pattern shapes such as heights and widths as parameters, whereby particular pattern shapes can be detected.

Figure 6A:
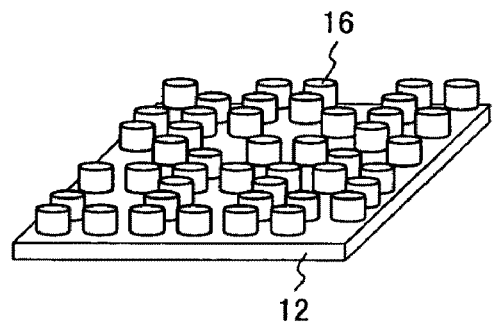
FIG. 6A is a diagram illustrating a shape of each pattern element included in a target pattern to be inspected.
Figure 6B:
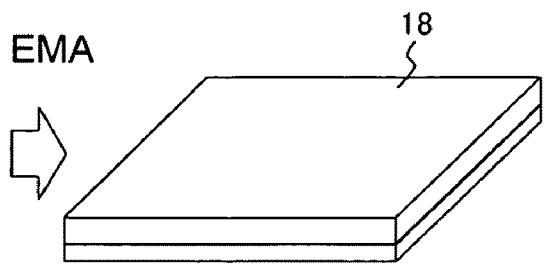
FIG. 6B is a diagram illustrating a state in which the target pattern to be inspected shown in FIG. 6A is expressed as one layer by the effective medium approximation.

As still another method, the shape of the target pattern element can be detected by use of Effective Medium Approximation (hereinafter referred to as "EMA"). First, the Effective Medium Approximation (EMA) will be described with reference to FIGS. 6A, 6B. A case where a target to be detected is formed of two media a (pattern 16) and b (air) as shown in the figure will be considered. In this case, if the area size of each medium is smaller than or equal to about one tenth of a wavelength of a light beam used for detection, it is no longer necessary to distinguish each medium from the other. Accordingly, the target to be detected can be considered as one layer 18 (refer to FIG. 6B). Here, on the assumptions that dielectric constants of the media are $\in_a$ and $\in_b$ respectively, and that an occupation ratio of the pattern is $f_a$, a dielectric constant $\in_c$ of the approximate layer 18 is expressed by an equation 1. Thus, the approximation of a layer, which is formed of a plurality of media, as a single medium layer is called "Effective Medium Approximation". Incidentally, the equation 1 of the effective medium approximation described above is taken as one example. Therefore, it is necessary to select the most suitable equation on the basis of a shape of a target and the quality of material thereof.

Equation 1

$$\varepsilon_c = \frac{\varepsilon_a \varepsilon_b + \chi \varepsilon_h (f_a \varepsilon_a + f_b \varepsilon_b)}{\chi \varepsilon_h + (f_a \varepsilon_b + f_b \varepsilon_a)} \quad (1)$$

$$\chi = (1-q)/q$$

Figure 7:
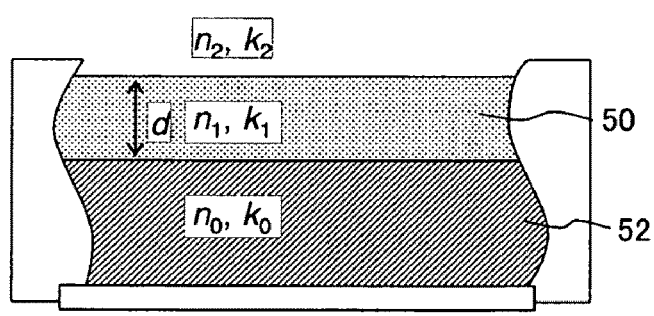
FIG. 7 is a schematic diagram illustrating an example of a single layer film.

$\in_a, \in_b, \in_c$: Complex dielectric constants
$f_a$: Occupation ratio
x: Shielding factor If the target is a film constituted of a single medium, the thickness of the film can be determined by detecting a spectral reflectance of a surface of the film. For example, a single layer film as shown in FIG. 7 will be considered. Here, if a refraction index n and an extinction coefficient k of a film 50 and those of a base 52 are known, a spectral reflectance of a film surface can be calculated by use of Fresnel's formula shown as an equation 2. Therefore, the film thickness can be determined by fitting the actually detected spectral reflectance to the reflectance determined by the Fresnel's formula with the film thickness used as a parameter.

Equation 2

$$|R|^2 = \left| \frac{r_2 + r_1 e^{-2\pi i 2 d_3 \frac{n-ik}{\lambda}}}{1 + r_1 r_2 e^{-2\pi i 2 d_3 \frac{n-ik}{\lambda}}} \right|^2 \quad (2)$$

$$r_q = \frac{(n_{q!} - ik_{q!}) - (n_{q-1} - ik_{q-1})}{(n_{q!} - ik_{q!}) + (n_{q-1} - ik_{q-1})}$$

n: Refraction index, k: Extinction coefficient,
d: Film thickness, λ: Wavelength,
$r_1, r_2$: Boundary reflectance between a base and a film, and a boundary reflectance between the film and air The relationship among the refraction index n, the extinction coefficient k, and the dielectric constant is expressed as an equation 3. Accordingly, the calculation of the film thickness by means of fitting can also be applied to a film that has been subjected to the effective medium approximation. In addition, if the occupation ratio $f_a$ is not known at the time of the effective medium approximation, the occupation ratio $f_a$ can also be concurrently determined by using the occupation ratio $f_a$ as a parameter at the time of fitting.

Equation 3

$$\in = \in_1 - i\in_2$$

$$\in_1 + n^2 + k^2$$

$$\in_2 = 2nk \quad (3)$$

Figure 8:
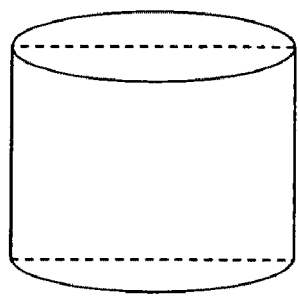
FIG. 8 is a schematic diagram illustrating a cylindrical pattern element.

$\in$: Complex dielectric constant,
n: Refraction index, k: Extinction coefficient Here, a pattern in which cylindrical pattern elements as shown in FIG. 8 are periodically arrayed will be considered. By means of the above-described effective medium approximation, the film thickness of an approximated layer, and an occupation ratio of a pattern portion to a nonpattern portion can be determined from the detected spectral reflectance of the surface.

In this case, if intervals between cylindrical pattern elements are known, the size of each cylindrical pattern element can be determined from the film thickness and the occupation ratio that have been determined. To be more specific, because a value of the determined film thickness is equivalent to a height value of the cylindrical pattern element, the height of the cylindrical pattern element can be determined. Moreover, because the occupation ratio is equivalent to an occupation ratio of the area occupied by the cylindrical pattern elements to the surface area, a diameter of each cylindrical pattern element can be determined by calculation.

Figure 9A:
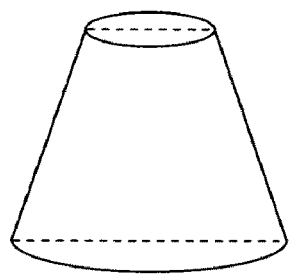
FIG. 9A is a diagram illustrating a pattern element whose cross-sectional shape is a trapezoid.
Figure 9B:
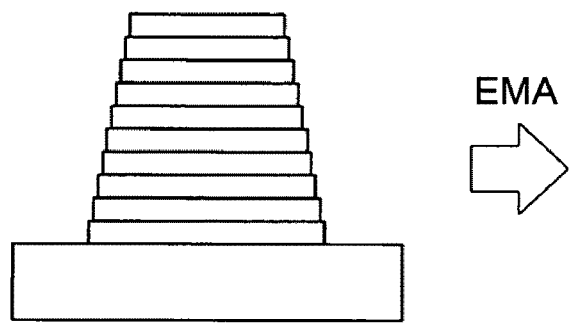
FIG. 9B is a diagram illustrating a state in which a pattern element is divided into a plurality of layers when a cross-sectional shape of the pattern element is a trapezoid.
Figure 9C:
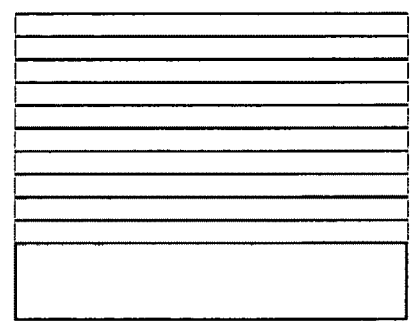
FIG. 9C is a diagram illustrating a pattern element shape acquired by applying the effective medium approximation to the plurality of layers shown in FIG. 9B, and then by superimposing the layers on one another.

Next, how to cope with a case where a cross-sectional shape of each pattern element is a trapezoid as shown in FIG. 9A will be considered. In such a case, each pattern element is divided into a plurality of layers as shown in FIG. 9B. Thus, by dividing each pattern element into a plurality of layers, each of which is subjected to the effective medium approximation, the film thickness of each layer, and an occupation ratio of a pattern portion to a nonpattern portion can be determined. As is the case with the cylindrical pattern element, on the assumption that a planar shape of each pattern element is a circle, the height and diameter of the pattern element in each layer can be determined from the film thickness and the occupation ratio, both of which have been determined for each layer. As a result, the whole shape of the pattern element can be determined by superimposing each shape formed by the height and diameter of the pattern element in each layer on one another.

Figure 10A:
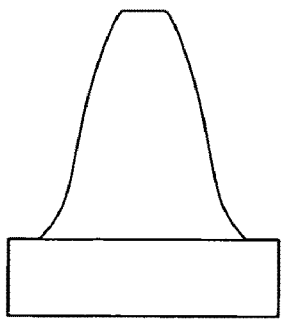
FIG. 10A is a diagram illustrating a pattern element whose cross-sectional shape is complicated.
Figure 10B:
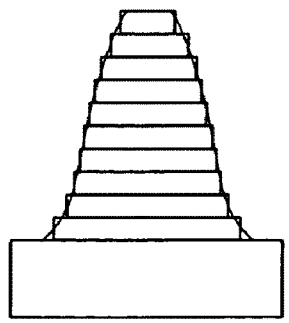
FIG. 10B is a diagram illustrating a state in which a pattern element is divided into a plurality of layers.
Figure 10C:
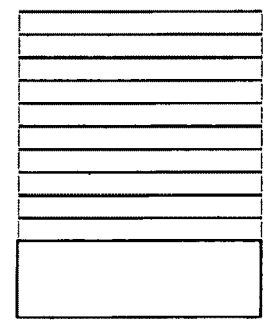
FIG. 10C is a diagram illustrating a pattern element shape acquired by applying the effective medium approximation to each of the layers into which the pattern element has been divided as shown in FIG. 10B, and then by superimposing the layers on one another.

In the example described above, a relatively simple shape is used. However, a similar method can also be applied to a pattern element having a complicated cross-sectional shape as shown in FIG. 10A. To be more specific, as shown in FIG. 10B, each pattern element is divided into a plurality of layers. Next, as shown in FIG. 10C, each of the divided layers is subjected to the effective medium approximation to determine an occupation ratio of a pattern portion to a nonpattern portion. On the assumption that a planar shape of each pattern element is a circle, the height and diameter of the pattern element in each layer is determined from the film thickness and the occupation ratio, both of which have been determined for the each layer. The whole shape of the pattern element can be determined by superimposing each shape formed by the height and diameter of the pattern element in each layer on one another.

The number of layers into which each pattern element is divided may be selected on the basis of the complexity of the each pattern element and the required precision. If the thickness of the divided layers is configured to be always the same, the amount of calculation required for the shape detection can be reduced. In addition, if a cross-sectional shape of each pattern element is approximated by a polynomial that is capable of expressing a shape by use of parameters, the number of which is smaller than the number of divided layers, the amount of calculation required for the shape detection can be reduced in like manner.

As described above, pattern elements, each of which has a size of several tens of nanometers, are formed on a disk medium that is a patterned medium. When a light beam whose wavelength ranges from 200 nm (deep ultraviolet light) to 800 nm (visible light) is used as a detection light beam, the pattern element size is about one-tenth the wavelength of the detection light beam. Accordingly, the above-described effective medium approximation can be applied to the patterned medium.

The above description is based on the assumptions that a planar shape of each pattern element, and intervals between the pattern elements, are known, and that a cross-sectional shape of each pattern element is symmetric. In the case of the patterned medium that is mainly targeted by the present invention, these assumptions hold. The reason why these assumptions hold will be described as below.

As described above, patterned media are manufactured by the nanoimprint technique, which is a prevailing method. The nanoimprint technique is a technique for transferring a pattern by embossing. Judging from characteristics of such an embossing process, intervals between pattern elements, and the planar shape of each pattern element, seldom vary on a transfer basis. Therefore, it can be thought that the intervals between pattern elements, and the planar shape of each pattern element, are known. Further, in a similar manner, judging from the characteristics of the embossing process, it can be assumed that a cross-sectional shape of each pattern element is also symmetric.

When the effective medium approximation is used, it can be thought that a target has a simple layered structure in comparison with a case where the electromagnetic wave analysis technique such as RCWA is used. Therefore, the amount of calculation can be reduced to a large extent. This method is advantageous as means for achieving high throughput.

It is to be noted that the above example describes the method for detecting a shape of a pattern element, which is formed on a disk, on the basis of a reflectance of a target surface. However, it is thought that there is a case where actual product inspection does not always require the detection of a shape of a pattern element. To be more specific, there is a case where inspection only requires a judgment as to whether or not a target is a non-defective item.

Next, a method for making a judgment only as to whether or not a target is a non-defective item will be described. As described above, FIG. 5 is a graph illustrating spectral reflectance of surfaces on which two patterns (a), (b) which differ in pattern element width are formed respectively. As shown in this figure, if a pattern element shape differs, a spectral reflectance of a surface also differs. Here, for example, on the assumption that (a) of FIG. 5 is normal, a judgment as to whether or not (b) is abnormal can be made by detecting a difference in spectrum waveform between the two patterns (a), (b).

As a method for detecting a difference in spectral reflectance, a judgment index value Delta (shown in an equation 4) is used. The judgment index value Delta indicates a difference between a reference waveform and a detected waveform. A judgment as to whether or not a shape of a pattern element is abnormal can be made by comparing this judgment index value with a predetermined threshold value. To be more specific, if the judgment index value is larger than or equal to the threshold value, a target is judged to be a defective item, whereas if the judgment index value is smaller than the threshold value, the target is judged to be a non-defective item.

Equation 4

$$\text{Delta} = \sqrt{\Sigma\{R_{standard}(\lambda) - R(\lambda)\}^2} \quad (4)$$

Figure 11:
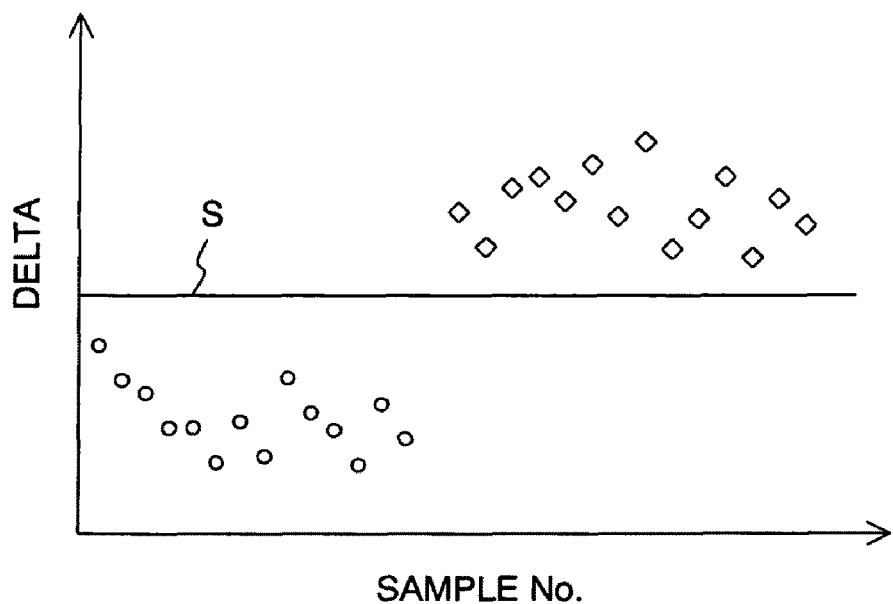
FIG. 11 is a graph illustrating an example of the distribution of judgment index values (Delta)

$R_{standard}$: Spectral reflectance of a normal pattern,
R: Detected spectral reflectance,
λ: Wavelength As an example of a method for determining a threshold value used for judgment, there is a method including the steps of: obtaining spectral reflectance with the width and height of a pattern element changed; calculating the judgment index value for spectral reflectance that should be judged to be normal, and the judgment index value for spectral reflectance that should be judged to be abnormal; and setting a threshold value S so that it is possible to discriminate between normal and abnormal states. FIG. 11 is a graph illustrating each judgment index value (marked with a circle in the figure) for spectral reflectance that should be judge to be normal, and each judgment index value (marked with a rhombus in the figure) for spectral reflectance that should be judge to be abnormal. As shown in FIG. 11, setting of the judgment threshold value S makes it possible to discriminate between normal and abnormal states.

Although it is desirable to adopt an actually detected spectral reflectance as the spectral reflectance used for threshold value settings, a spectral reflectance which is created by optical simulation can also be adopted.

In addition, judging from FIG. 5, it is understood that a change in reflectance measured when the wavelength is 400 nm or less is larger than that measured when the wavelength exceeds 400 nm. For this reason, detection of a spectral reflectance in a wavelength range of ultraviolet rays is advantageous from the viewpoint of the sensitivity required when a shape and an abnormal state are detected.

Usually, the wavelength of a light beam which can be detected in the air is about 200 nm. Therefore, it is more realistic to detect a light beam whose wavelength is about 200 nm or more from a practical standpoint. As a matter of course, if detection is performed within a wavelength range of 200 nm or less, it is more advantageous from the viewpoint of the sensitivity required when a shape and an abnormal state are detected.

Moreover, judging from FIG. 5, it is thought that a change in spectral reflectance is relatively large in a wavelength range in which a reflectance is large. Therefore, there is also considered a method in which an optical constant of a target pattern is evaluated beforehand, and detection is mainly performed in a wavelength range in which a reflectance becomes larger. Because a target to be detected has a multilayer structure, in consideration of not only an optical constant of a surface material but also interference in the multilayer structure, it is necessary to select a wavelength range in which an apparent reflectance becomes larger. Because detection of the wavelength at which a spectral reflectance becomes the maximum suffices, the number of wavelengths to be detected is from about 3 to about 20 although the number of wavelengths to be detected depends on the structure of the target, and the quality of material of the target.

The above example describes the method in which calculated data of spectral reflectance is used. However, as another method, non-defective items or reference data may also be actually detected beforehand so that the non-defective items or the reference data can be used instead of the calculated data of spectral reflectance.

Figure 12:
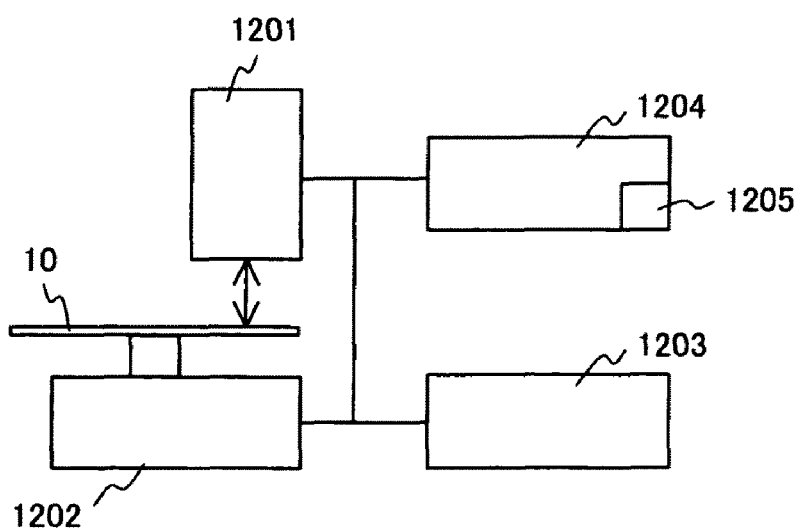
FIG. 12 is a schematic diagram illustrating a configuration of a hard disk inspection apparatus.

Next, a hard disk inspection apparatus which uses the above-described detection method will be described. FIG. 12 is a diagram illustrating a configuration of a hard disk inspection apparatus according to this embodiment. The hard disk inspection apparatus according to this embodiment includes: a spectral detection optical system 1201 for irradiating, with a detection light beam, a hard disk medium 10 that is a target to be inspected, and then for performing spectral detection of a reflected light beam from the hard disk medium 10; a stage unit 1202 that holds the hard disk medium 10 which is the target to be inspected, and that can change a position relative to the spectral detection optical system 1201 so that the spectral detection can be performed at an arbitrary position on the hard disk medium; a control unit 1203 for controlling the operation of the spectral detection optical system and that of the stage unit; and a data processing unit 1204 for detecting a shape of a pattern element formed on a target surface, or an abnormal state of the shape, on the basis of spectral detection data. The data processing unit 1204 is provided with a display unit 1205.

Figure 13:
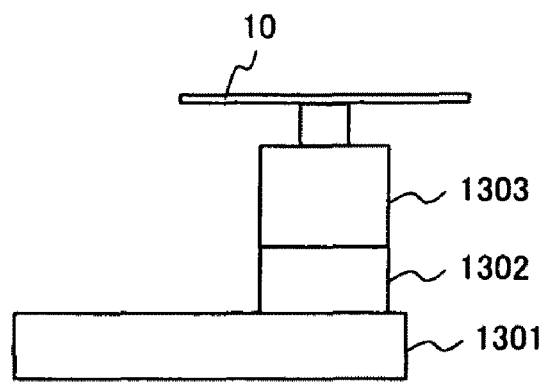
FIG. 13 is a schematic diagram illustrating an example of a stage unit.

FIG. 13 is a schematic diagram illustrating an example of the stage unit 1202. As shown in this figure, the stage unit 1202 includes: an X stage 1301 that moves in a direction parallel to a surface of the disk; a Z stage 1302 that moves in a direction perpendicular to the surface of the disk; and a θ stage 1303 for rotating the disk.

The Z stage 1302 is used to move the target disk to be inspected 10 to a focus position of the optical system. The X stage 1301 and the θ stage 1303 are used to move the spectral detection optical system 1201 to an arbitrary position on the surface of the target disk to be inspected 10. As a method for moving the spectral detection optical system 1201 to an arbitrary position on the surface of the target disk to be inspected, there is also considered a method that uses an XY stage. However, because the target to be inspected is a disk, and because a pattern element, which is the target to be inspected, is also formed in a concentric circular shape or on a concentric circle, an Xθ stage is more suitable than the XY stage. In addition, for example, when the whole surface of the disk is inspected at high speed, the Xθ stage is more suitable than the XY stage because the operation of the Xθ stage is simpler than that of the XY stage.

Figure 14:
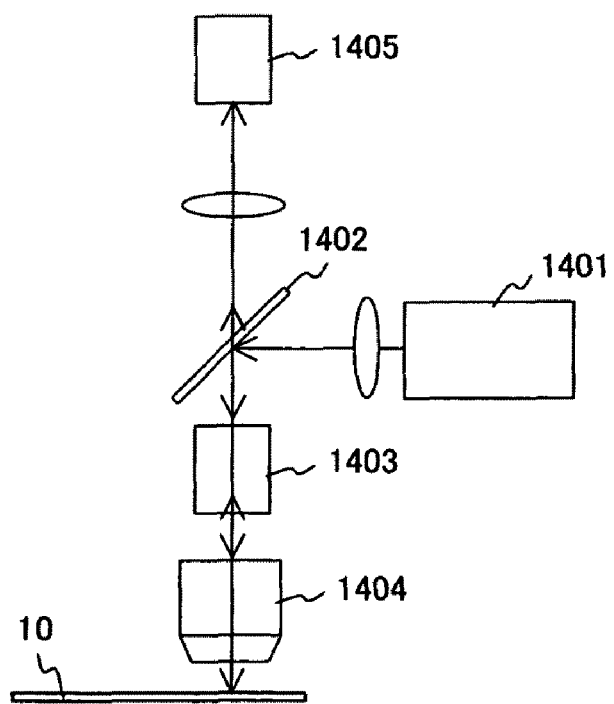
FIG. 14 is a schematic diagram illustrating an example of a spectral detection optical system.

FIG. 14 is a diagram illustrating a specific example of the spectral detection optical system 1201 shown in FIG. 12. As shown in the figure, the spectral detection optical system 1201 mainly includes a light source 1401, a half mirror 1402, a polarizer 1403, an objective lens 1404, and a spectrometer 1405. A direction of a light beam emitted from the light source 1401 is changed by the half mirror 1402. The light beam then passes through the polarizer 1403 and the objective lens 1404. As a result, the target disk to be inspected 10 is irradiated with the light beam. A reflected light beam from the target disk to be inspected 10 passes through the objective lens 1404 and the polarizer 1403 again. The reflected light beam is then introduced to the spectrometer 1405.

At this time, if an entrance position of the spectrometer 1405 is set at an image formation position, an area in which the spectral detection is performed can be limited by a shape of an entrance. For example, on the assumptions that the size of the entrance is φ200 μm, and that the magnification on an imaging surface is 20 times, the size of a spectral detection area is φ10 μm on the target disk to be inspected.

As described above, when a light beam having a wavelength of about 200 nm is used, applicable optical elements are limited. As the light source 1401, a light source for emitting a light beam whose wavelength is about 200 nm or more (for example, a xenon lamp and a deuterium lamp) can be used. However, there is also a case where even a light source whose wavelength is about 400 nm or more can achieve sufficient performance depending on a target to be inspected. In this case, a light source for emitting a light beam whose wavelength range is from visible light to infrared rays may also be used (for example, a halogen lamp).

The optical system according to this embodiment uses a reflective objective lens as the objective lens 1404. There are very few refractive objective lenses, each of which is formed of a generally used lens, and each of which can broadly cover light beams from a light beam whose wavelength is about 200 nm up to visible light. The reflective objective lens is formed of a mirror. The reflective objective lens can be used for a light beam whose wavelength ranges from about 200 nm.

Spectroscopes on the market, which are produced by ZEISS, Hamamatsu Photonics K.K., and the like, can be used as the spectrometer 1405. These spectroscopes can be used for a light beam whose wavelength ranges from about 200 nm.

Figure 15:
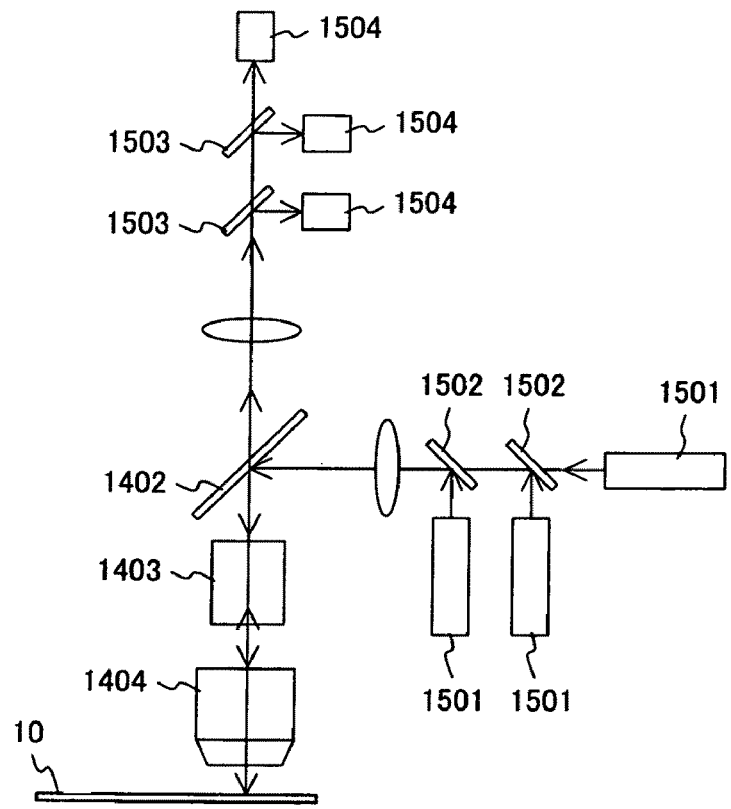
FIG. 15 is a schematic diagram illustrating another example of a spectral detection optical system.

In the above description, a light beam whose wavelength range is broad is subjected to the spectral processing. However, a method for detecting a light beam having a plurality of discrete wavelengths can also be considered. For example, as shown in FIG. 15, there is a method including the steps of: focusing light beams from a plurality of laser-beam light sources 1501 on the same optical axis by use of a plurality of dichroic mirrors 1502 to make a detection light beam; separating a reflected light beam from a disk into a plurality of light beams by use of a plurality of dichroic mirrors 1503 in a similar manner; and detecting the separated light beams by the plurality of spectrometers 1504. Although FIG. 15 shows a case where three laser-beam light sources are used, the number of discrete wavelengths is not limited to three.

Figure 16:
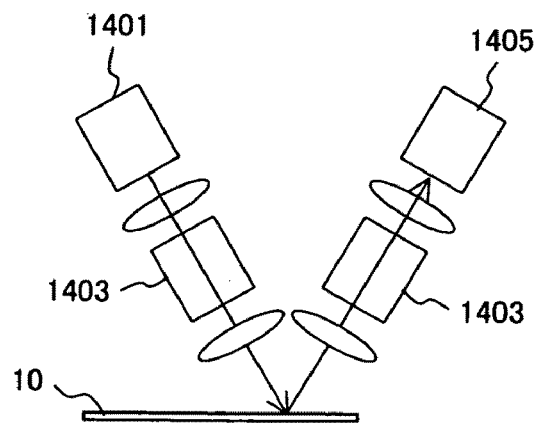
FIG. 16 is a schematic diagram illustrating still another example of a spectral detection optical system.

In addition, the above-described example shows the method in which a detection light beam is emitted in a vertical direction so that a regular reflected light beam thereof is detected. However, for example, as shown in FIG. 16, even a method in which a light beam is emitted in an oblique direction so that a regular reflected light beam thereof is detected can also produce the same effects. The oblique incidence makes it possible to achieve the higher precision in detection of a shape of a pattern and in detection of a defect of the pattern element although it depends on a shape of a target, and the structure and material thereof.

Figure 1:
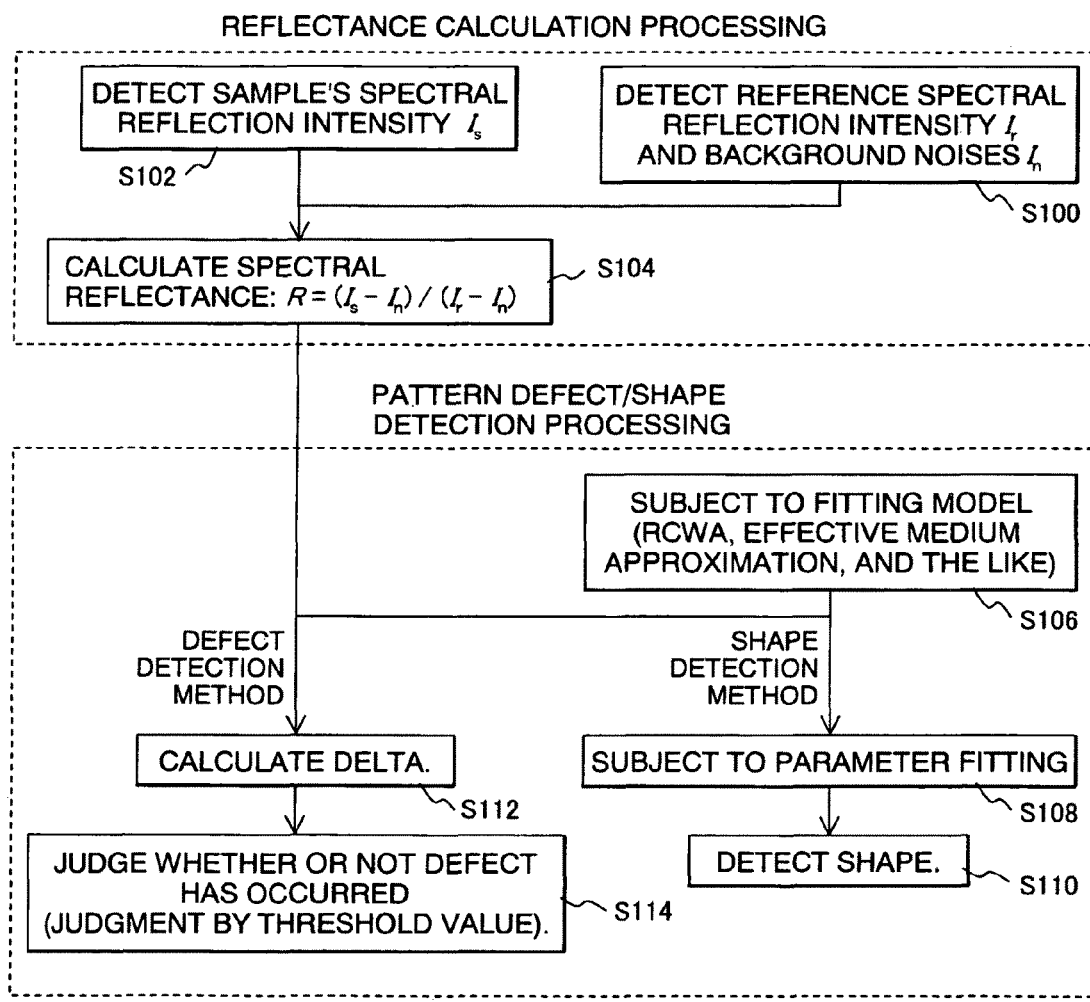
FIG. 1 is a diagram illustrating data processing performed by a detection method for detecting a shape of a pattern element and a defect in the shape of the pattern element.
Figure 2:
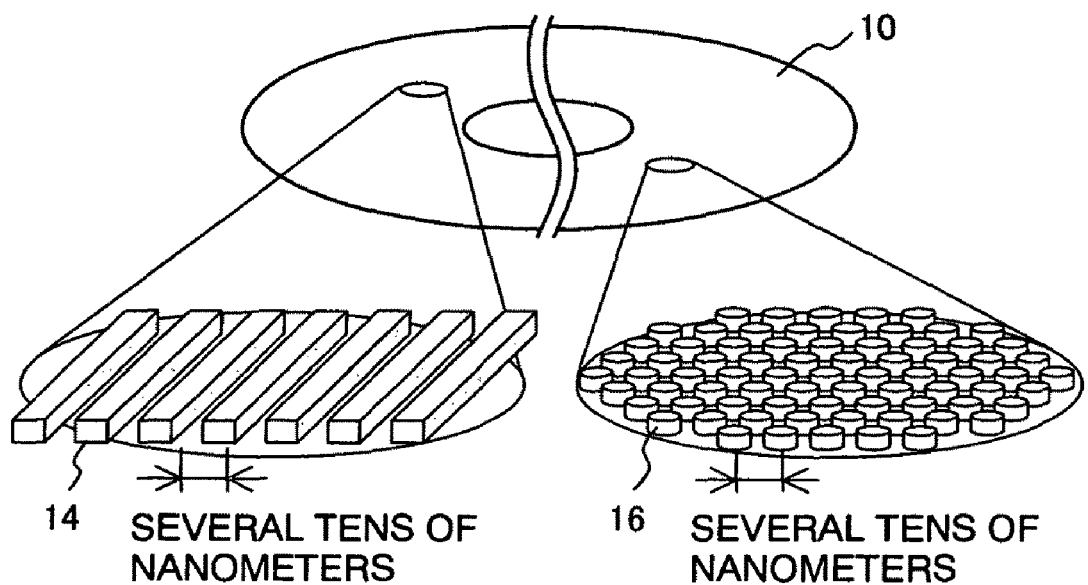
FIG. 2 is a schematic diagram illustrating an example of a patterned medium.

As shown in FIG. 1, roughly classifying, the data processing unit 1204 executes two kinds of processing as follows: one is calculation of a reflectance; and another is detection processing of detecting a shape of a pattern element, and a defect in the shape of the pattern element. As described above, according to the present invention, a shape of a target pattern element to be inspected, and a defect in the shape of the target pattern element, are detected on the basis of a spectral reflectance of a target surface to be inspected. However, what can be detected by the above-described optical system is spectral reflection intensity distribution of the target surface to be inspected. For this reason, the spectral reflection intensity distribution of a mirror surface Si is detected beforehand (S100). Then, a ratio of the spectral reflection intensity (S102) of the target surface to be inspected to the spectral reflection intensity distribution is used. To be more specific, a relative spectral reflectance is used (S104). When the ratio is determined, there is a case where background noises $I_n$ overlap spectral reflection intensity data $I_s$ depending on a detector. Therefore, the background noises $I_n$ are also detected beforehand. When the relative reflectance is calculated, the background noises $I_n$ are subtracted from the spectral reflection intensity data Is. The relative spectral reflectance which has been calculated in this manner is subjected to the above-described pattern shape detection processing (S106, S108, S110) and the above-described defect detection processing (S112, S114). As a result, a shape of the pattern element, and a defect in the shape of the pattern element, can be detected. In FIG. 1, both the defect detection and the shape detection are described. However, performing any one of them as occasion demands suffices.

Figure 17:
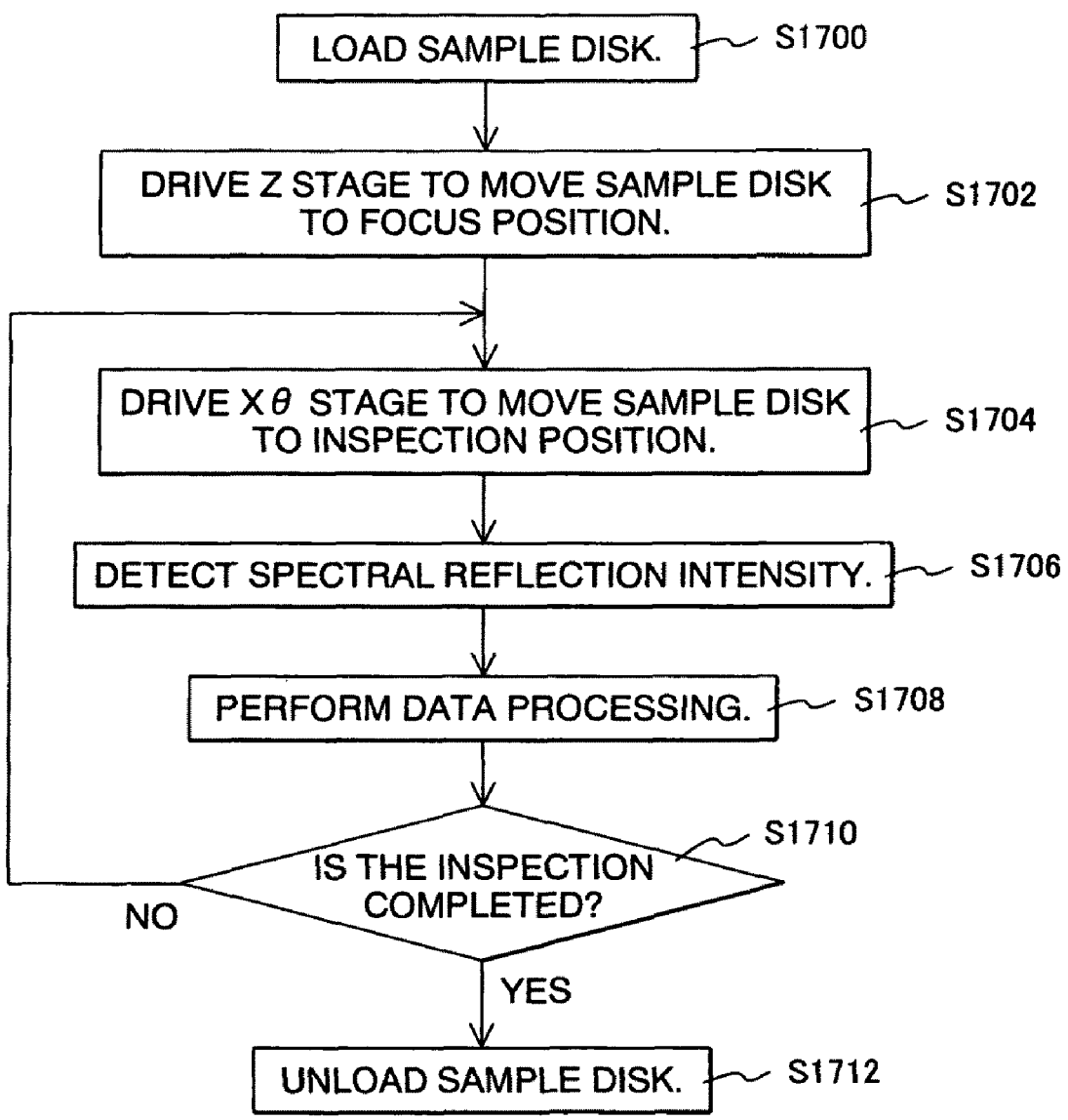
FIG. 17 is a flowchart illustrating the operation of a hard disk inspection apparatus.

Next, how the inspection apparatus operates will be described with reference to FIG. 17. First, a target disk to be inspected is placed on a stage (S1700). The center and direction of the target disk to be inspected 10 is detected (aligned) beforehand if necessary. Next, the Z stage 1302 is driven to move the target disk to be inspected 10 to a focus position of the spectral detection optical system 1201 (S1702). Subsequently, the X stage 1301 and the θ stage 1303 are driven to move the target disk to be inspected 10 to such a position that inspection can be performed immediately under the spectral detection optical system 1201 (S1704). Here, the spectral reflection intensity of the surface of the target disk to be inspected 10 is detected (S1706). A shape of a pattern element, and a defect in the shape of the pattern element, are then detected by the data processing unit 1204 (S1708). The movement of these stages, the spectral detection, and the data processing are repeated. After the inspection ends (S1710), the target disk to be inspected is removed (S1712). Incidentally, description of the alignment of the disk, and description of the placing/removal of the disk to/from the stage, are omitted.

If the inspection is executed with each of the X stage 1301 and the θ stage 1303 consecutively operated, a helical area on the disk can be inspected. For example, if the X stage 1301 is moved by a distance equivalent to the detection spot size while the θ stage 1303 makes one turn, the whole surface of the disk can be inspected.

Figure 18:
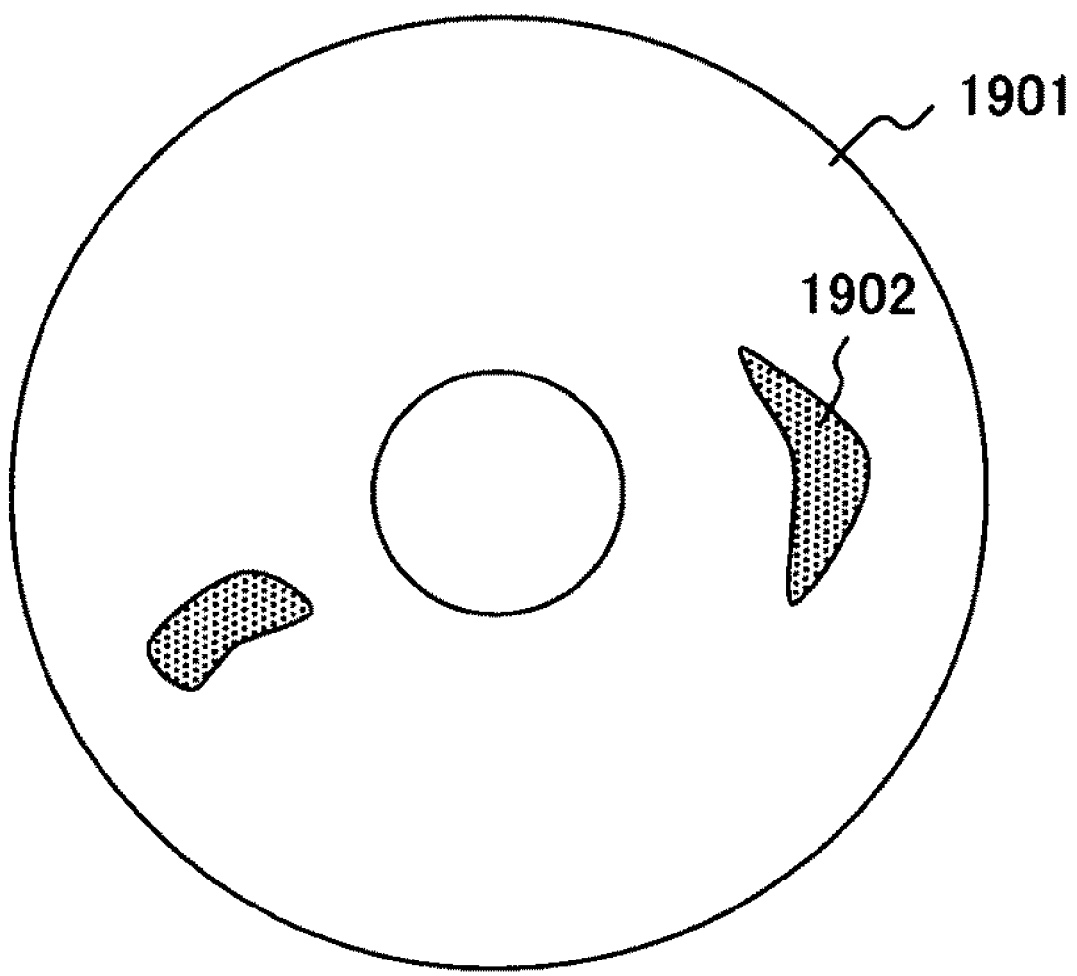
FIG. 18 is a diagram illustrating an example in which the result of the shape/defect detection is displayed as the distribution.

When the whole surface of the disk is inspected as described above, the result of detecting the shape and the defect can be displayed, as the distribution, on the display unit 1205 of the data processing unit as shown in FIG. 18. FIG. 18 is a diagram two-dimensionally illustrating a shape defect area 1902 as the distribution on a disk image 1901. Similarly, parameters each indicating a shape of a pattern element such as the width and height of the pattern element may also be three-dimensionally displayed.

As a result of the above processing, the inspection apparatus according to this embodiment makes it possible to detect the distribution of the shape and defect of each pattern element formed on, for example, a patterned medium. The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. An inspection method for inspecting a hard disk medium, said method comprising the steps of:
    irradiating a surface of the hard disk medium with a light beam including a plurality of wavelengths, thereby forming pattern elements with regular intervals on the hard disk medium;
    detecting the intensity, on a wavelength basis, of a light beam reflected from the hard disk medium;
    calculating a spectral reflectance from the detected intensity of the reflected light beam;
    detecting a shape of a pattern element formed on the hard disk medium on the basis of the calculated spectral reflectance, including comparing the calculated spectral reflectance with a predetermined spectral reflectance, the predetermined spectral reflectance created by using an effective medium approximation based on the shape of the target to be inspected and the quality of material thereof; and
    wherein when the effective medium approximation is used, a target pattern element is divided into a plurality of layers as in a multilayer film structure, and each of the plurality of layers is subjected to the effective medium approximation.

2. The inspection method for inspecting the hard disk medium according to claim 1,
    wherein when the effective medium approximation is used, a planar shape of the target pattern element, a cross-sectional shape thereof, and intervals between pattern elements are used as parameters of the effective medium approximation.

3. The inspection method for inspecting the hard disk medium according to claim 1,
    wherein said step of detecting the shape of the pattern element includes a step of calculating a height and a diameter of the pattern element based on an interval between the pattern elements, the calculated film thickness, and an occupation ratio.

4. An inspection method for inspecting a hard disk medium, said method comprising the steps of:
    irradiating a surface of the hard disk medium with a light beam including a plurality of wavelengths, thereby forming pattern elements with regular intervals on the hard disk medium;
    detecting the intensity, on a wavelength basis, of a light beam reflected from the hard disk medium;
    calculating a spectral reflectance from the detected intensity of the reflected light beam; and
    comparing the calculated spectral reflectance with a predetermined spectral reflectance, thereby determining whether or not a shape of a pattern element formed on the hard disk medium is defective;
    wherein the predetermined spectral reflectance is created based on an effective medium approximation, including a shape of a target to be inspected and a quality of material thereof; and
    wherein when the effective medium approximation is used, a target pattern element is divided into a plurality of layers as in a multilayer film structure, and each of the plurality of layers is subjected to the effective medium approximation.

5. The inspection method for inspecting the hard disk medium according to claim 4,
    wherein said step of determining whether or not the shape of the pattern element is defective includes a determination as to whether or not a pattern element exists.

6. The inspection method for inspecting the hard disk medium according to claim 4, wherein
    said step of determining whether or not the shape of the pattern element is defective further includes the steps of:
        determining the difference between a spectral reflectance of a predetermined non-defective item and the calculated spectral reflectance, and either of:
        determining that the shape of the pattern element is nondefective if the determined difference is smaller than or equal to a predetermined threshold value, or
        determining that the shape of the pattern element is defective if the determined difference is larger than the predetermined threshold value.

7. The inspection method for inspecting the hard disk medium according to claim 4,
    wherein said step of detecting the shape of the pattern element includes a step of calculating a height and a diameter of the pattern element based on an interval between the pattern elements, the calculated film thickness, and an occupation ratio.

8. The inspection method for inspecting the hard disk medium according to claim 6, wherein
the threshold value used in the step of determining whether or not the shape of the pattern element is defective is set at a value that can discriminate between a spectral reflectance associated with the determination that the shape of the pattern element is nondefective, and a spectral reflectance associated with the determination that the shape of the pattern element is defective.

9. An inspection apparatus for inspecting a hard disk medium, said inspection apparatus comprising:
irradiation means for irradiating a surface of the hard disk medium with a light beam including a plurality of wavelengths, thereby forming pattern elements with regular intervals on the hard disk medium;
spectral detection optical means for detecting the intensity of a reflected light beam from the surface of the hard disk medium on a wavelength basis;
means for holding the hard disk medium, and for moving the hard disk medium or the spectral detection optical means so that the spectral detection optical means can detect the intensity of the reflected light beam at an arbitrary position on the surface of the hard disk medium; and
a data processing unit for calculating a spectral reflectance from the intensity of the reflected light beam detected by the spectral detection optical means, and for detecting a shape of a pattern element formed on the hard disk medium, thereby determining whether or not the shape is defective by comparing the calculated spectral reflectance with a predetermined spectral reflectance created by using an effective medium approximation based on a shape of a target to be inspected, and a quality of material thereof;
wherein when the effective medium approximation is used, a target pattern element is divided into a plurality of layers as in a multilayer film structure, and each of the plurality of layers is subjected to the effective medium approximation.

10. The inspection apparatus for inspecting the hard disk medium according to claim 9,
wherein said spectral detection optical means includes a dichroic mirror for separating a reflected light beam on a wavelength basis.

11. The inspection apparatus for inspecting the hard disk medium according to claim 9,
wherein the number of wavelengths detected by the spectral detection optical means, and used to determine the intensity of the reflected light beam, ranges from 3 to 20.

12. The inspection apparatus for inspecting the hard disk medium according to claim 9,
wherein said irradiation means for irradiating the surface of the hard disk medium with the light beam including the plurality of wavelengths irradiates the surface with the light beam in a direction perpendicular to, or diagonal to, the surface of the hard disk medium.

13. The inspection apparatus for inspecting the hard disk medium according to claim 9,
wherein said means for moving the hard disk medium or the spectral detection optical means includes at least a uniaxial direct acting mechanism and a rotating mechanism.

14. The inspection apparatus for inspecting the hard disk medium according to claim 9,
wherein a light beam whose wavelength falls within an ultraviolet range is used as the light beam including the plurality of wavelengths.

15. The inspection apparatus for inspecting the hard disk medium according to claim 9,
wherein the light beam including the plurality of wavelengths includes a wavelength for which a refraction index, or an apparent refraction index, of the target pattern element is large.

16. The inspection apparatus for inspecting the hard disk medium according to claim 9,
wherein the light beam including the plurality of wavelengths includes a wavelength for which a change in shape of the pattern element formed on the hard disk medium causes the intensity of the reflected light beam to change to the maximum extent.

17. The inspection apparatus for inspecting the hard disk medium according to claim 9,
wherein said data processing unit includes a display unit configured to two-dimensionally display or three-dimensionally display the distribution of parameters on the display unit on the basis of the result of the determination, the parameters indicating a shape of a pattern element and a defect in the shape.

18. The inspection apparatus for inspecting the hard disk medium according to claim 9,
wherein the data processing unit calculates a height and a diameter of the pattern element based on an interval between the pattern elements, the calculated film thickness, and an occupation ratio.

* * * * *